United States Patent [19]

Ford, Jr. et al.

[11] Patent Number: 5,392,659
[45] Date of Patent: Feb. 28, 1995

[54] APPARATUS FOR PROVIDING MULTIPLE SAMPLES OF MATERIAL FROM A MOVING CONVEYOR

[75] Inventors: James J. Ford, Jr., Cincinnati, Ohio; David W. Beitz, Burlington, Ky.; Michael J. Nagle, Jr., Hamilton, Ohio

[73] Assignee: Tema Systems, Inc., Cincinnati, Ohio

[21] Appl. No.: 57,535

[22] Filed: May 4, 1993

[51] Int. Cl.⁶ .................. G01N 1/08; G01N 1/12; G01N 1/20
[52] U.S. Cl. .................. 73/863.53; 73/863.01; 73/863.56; 73/863.91
[58] Field of Search ........... 73/863.56, 863.01, 863.52, 73/863.53, 864.32, 863.91, 863.92, 863.55

[56] References Cited

U.S. PATENT DOCUMENTS

| | | | |
|---|---|---|---|
| 3,373,615 | 3/1968 | Silver et al. | 73/863.53 |
| 3,524,352 | 8/1970 | Paul | 73/863.53 |
| 3,541,862 | 11/1970 | Jordison | 73/863.53 |
| 3,791,218 | 2/1974 | Pennington | 73/863.91 X |
| 4,133,210 | 1/1979 | Jaeger | 73/863.91 X |
| 4,574,645 | 3/1986 | Allen et al. | 73/863.56 X |
| 5,115,688 | 5/1992 | Van der Merwe et al. | 73/863.91 |

FOREIGN PATENT DOCUMENTS

| | | | |
|---|---|---|---|
| 752634 | 12/1970 | Belgium | 73/863.53 |
| 977578 | 11/1975 | Canada | 73/863.91 |
| 1381133 | 1/1975 | United Kingdom | 73/863.53 |
| 199501 | 7/1967 | U.S.S.R. | 73/863.53 |
| 742752 | 6/1980 | U.S.S.R. | 73/863.91 |
| 828005 | 5/1981 | U.S.S.R. | 73/863.91 |

OTHER PUBLICATIONS

Brochure entitled "Sampling Systems" by Tema Systems Inc. printed in 1991 9 pages.

Primary Examiner—Thomas P. Noland
Attorney, Agent, or Firm—Wood, Herron & Evans

[57] ABSTRACT

A sampling machine for moving a sampling scoop through bidirectional full rotations which are effective to remove multiple sample volumes from a moving conveyor. The sampling scoop has a home position which is maintained by the its drive without requiring a separate brake. A programmable control provides a full range of multiple sampling cycles at high sampling rates. The sampling scoop cavities are comprised of three straight flat surfaces including a pusher surface which is substantially vertical as the sample volume is pushed off an edge of the moving conveyor.

19 Claims, 3 Drawing Sheets

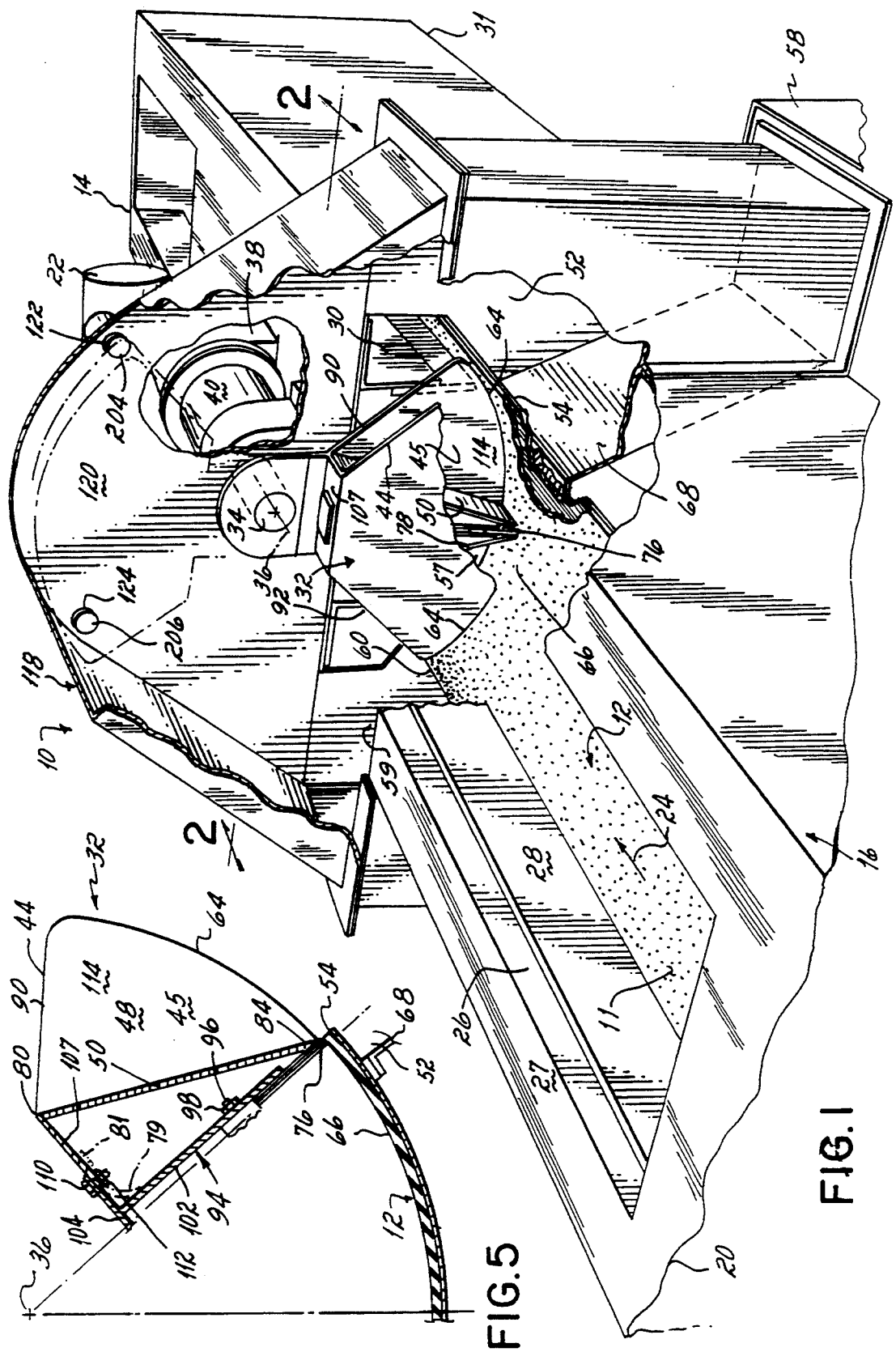

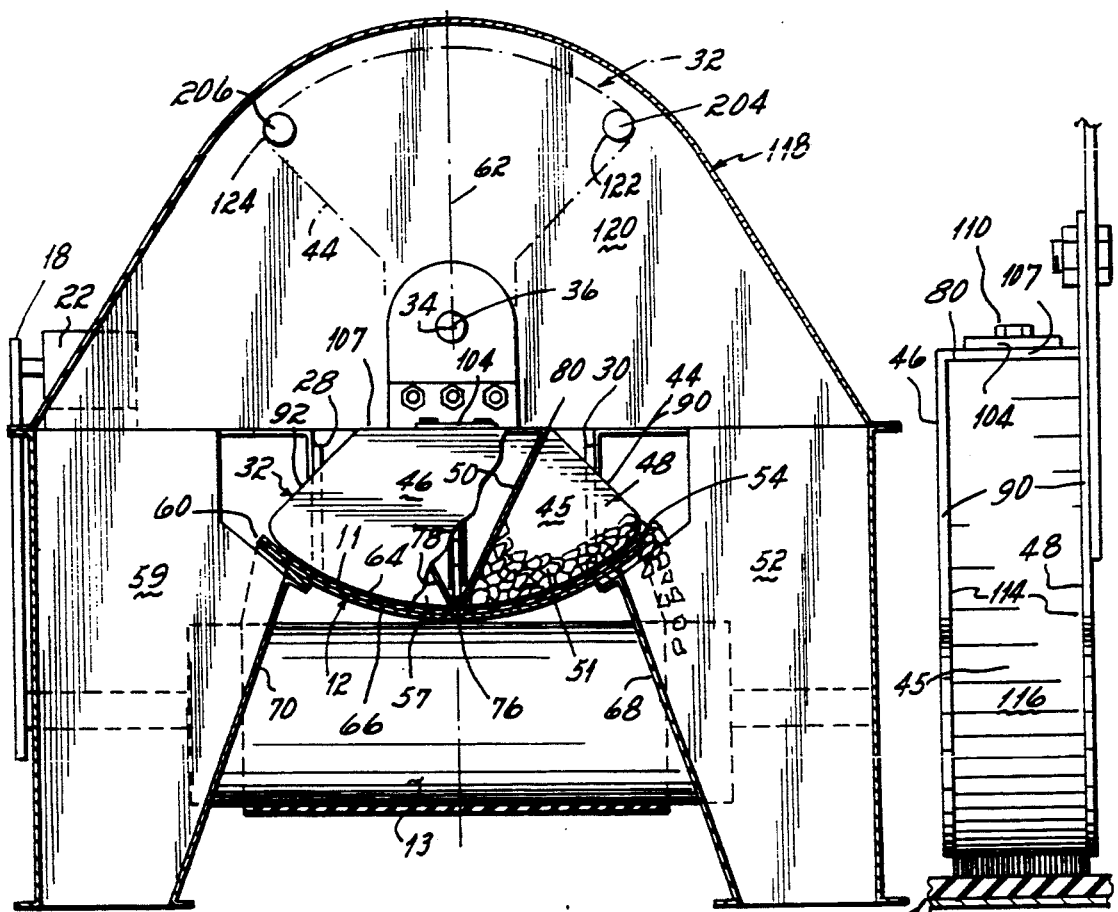

APPARATUS FOR PROVIDING MULTIPLE SAMPLES OF MATERIAL FROM A MOVING CONVEYOR

BACKGROUND OF THE INVENTION

1. Field of the Invention

The present invention relates generally to the area of sample taking and more particularly to an apparatus for removing multiple sample volumes of a material from a moving conveyor.

2. Description of the Related Art

In processing mined materials, for example, coal, the coal is moved along a series of conveyors through and between various processing stages and stations. Further, as the coal moves through different processing points, at each point, the coal will have a unique combination of physical characteristics that make it suitable for particular applications. Other applications may require additional processing, for example, additional crushing, sizing, washing and other step to improve quality. As the coal is processed to a point that it is suitable for a particular application, some of the coal is diverted for final processing and testing prior to transportation.

For each application, the coal is tested against quality standards associated with that application. Therefore, as coal intended for a particular application is conveyed, a primary sample volume of the coal is periodically removed from the conveyor. That primary sample is further conveyed to another station where a generally smaller secondary sample volume is periodically taken. Those secondary samples are collected and analyzed as a representation of the composite of the total load.

The sample quantities and sampling frequency associated with each application, or use, of the coal are determined by industry standards which, for example, may be set by the American Society of Testing Materials (ASTM). After the coal samples are collected, the samples are then tested to determine qualitative variables such as sulfur content, ash, BTU content, etc., to confirm that the coal complies with the standards established for its intended application or use. The samples and test results are often forwarded to the customer so that the customer can compare the sample analysis against the actual shipment of coal received.

A total shipment of coal may be up to generally 10,000 tons or 100 rail cars. While having a composite sample of all 10,000 tons is helpful, all 10,000 tons are not identically homogeneous with regard to their qualitative characteristics. Therefore, if there is a discrepancy found in the sample, it is very difficult to associate that discrepancy with a particular quantity of the total 10,000 ton load. Therefore, it is the practice to obtain multiple samples from any particular load. For example, a first sample may be taken that represents a composite of all 10,000 tons or 100 rail cars comprising the total quantity of coal sold. Further, additional samples may be taken which represent a composite sample of a fraction of the total load such as, for example, 500 tons or 5 rail cars. Therefore, if qualitative discrepancies are found, they may be more easily associated with a particular portion of the total load.

Various mechanisms currently exist for removing samples of material, such as coal, from a moving conveyor. The assignee of the present invention has marketed several different coal samplers. For example, one sampler has a sampling scoop connected to a unidirectional rotating drive shaft coupled through a gear drive to an AC motor. A mechanical brake holds the scoop in a park, or home, position at which the centerline of the scoop is above the axis of rotation at a 10 o'clock position. In response to a sample command, the brake releases the drive, and the AC motor rotates the scoop one complete revolution. As the scoop passes transversely over the moving conveyor, a predetermined volume of coal is collected and pushed off the conveyor into a collection chute. The bottom edge of the scoop is curved at a radius equal to the distance from the axis of rotation to the bottom edge, and the moving conveyor is curved to match the curvature of the bottom edge of the scoop.

Other coal sampling mechanisms are known such as, for example, those available from J. B. Long, of Knoxville, Tenn. They market a sampler which is movable bidirectionally but not through a full revolution. The sampling scoop is held by a brake in a first home position located approximately at the 10 o'clock position on a first side of the conveyor. The scoop is pneumatically driven and pivots across the conveyor to a second home position located approximately at the two o'clock position adjacent the other side of the conveyor. That pivoting motion pushes a coal sample off the other side of the conveyor. A mechanical brake also holds the scoop at the second home position. When the scoop is pivoted in the opposite direction to the 10 o'clock position first home position, it pushes a coal sample off the first side of the conveyor. If only a single sample is required, the scoop is pivoted in one direction for example, from the ten o'clock first home position to the two o'clock second home position. In order to return the scoop to the 10 o'clock first home position, the sampling scoop must be lifted vertically, it is then pivoted from above the two o'clock second home position to a position above the ten o'clock first home position. Therefore, the pivoting motion does not interfere with coal traveling on the conveyor. When above the 10 o'clock first home position, the sampling scoop is then moved vertically downward to the first home position.

The above devices have the disadvantage of having to use a brake to hold the scoop at the home positions. One of the devices requires additional mechanisms to lift and lower the scoop in order to provide a unidirectional operation to collect a single composite of samples. In addition, pneumatic devices are relatively slow which means the time between samples is relatively long.

An AC motor drive has a disadvantage in that it is less tolerant to a high sample rate requiring a high frequency of direction reversals.

SUMMARY OF THE INVENTION

To overcomes the disadvantages associated with prior sampling devices, the present invention provides a bidirectional full rotational material sampler having a home position which can be maintained without the use of a separate brake, for example, a 12 o'clock position. The invention is especially suited for collecting precise multiple composite sample volumes from a moving conveyor at secondary, tertiary, quaternary or other sampling stations.

According to the principles of the present invention and in accordance with the described embodiment, the sampler is mounted above a moving conveyor. A sampling scoop is connected to a horizontal drive shaft from a gear drive such that the sampler has approximately 360° of rotational motion that sweeps transverse to the direction of motion of the moving conveyor. Therefore, the sampling scoop starts and stops at a home, or park position, for example, a 12 o'clock position. The sampling scoop has a curved lower edge defined by a radius extending from the axis of rotation, along a centerline of the scoop and terminating at the lower edge. The shape of the moving conveyor changes from a generally flat surface to a curved surface matching the curve of the lower edge of the scoop.

The sampler has a sampling scoop with dual material collection cavities, each having three straight smooth surfaces including a sampler pusher wall that is substantially vertical as it passes an edge of the conveyor. Therefore, the cavity empties completely after each sampling cycle, thereby providing precise and uniform sample volumes. The sampling scoop further contains a brush located between the opposed cavities and extending radially downwardly from the lower edge of the scoop. As the scoop moves transversely across the moving conveyor the leading cavity fills with a sample of coal, and the trailing brush wipes fine particles of coal from the conveyor which are not picked up by the scoop. As the scoop rotates past the edge of the conveyor the sampled coal in the cavity and in front of the brush is discharged into a chute. The sample continues through its rotational movement and stops at the home position which is typically close to its highest point of the rotation. At that position, the sampling scoop is above the axis of rotation; and its centerline is approximately vertical.

The gear drive is connected to a DC motor with dynamic and regenerative braking. In response to a sample command, the DC motor is operated at maximum velocity to rotate the scoop from the home position at maximum velocity transversely across the conveyor until the leading edge of the scoop is detected by a first position sensor. In response thereto, the motor controller commands the motor to move at a lesser velocity; and the dynamic braking of the motor is applied. A decelerating rotation of the scoop continues until its leading edge is detected by a second proximity sensor which is effective to terminate the velocity command signal to the motor. Regenerative braking is applied to stop the sampling scoop at the home position. That home position is maintained by the mechanical resistance of the motor and drive and no mechanical brake is used. The motor control is effective to selectively rotate the scoop in either rotational direction through the same cycle. Further, the control permits any number of rotations in one direction in between successive rotations in the opposite direction.

The construction of the present invention has the advantage of maintaining the scoop at the home position without the requirement of a separate brake. A further advantage is that the scoop may be rotated in either direction without the requirement of additional mechanisms or controls. The surfaces bounding the cavities of the scoop are straight and smooth so that the material being sampled does not accumulate or build-up in the cavity as a result of the sampling process. Further, the DC motor and its motor control are capable of providing high sampling frequencies.

These and other objects of the present invention will become more readily apparent during the following detailed description in conjunction with the drawings herein.

BRIEF DESCRIPTION OF THE DRAWINGS

FIG. 1 is a perspective view, partially cut away, of the sampling apparatus in conjunction with a moving conveyor.

FIG. 2 is a center cross-sectional view taken along line 2—2 of FIG. 1 and illustrates the scoop traversing the moving conveyor, and the home position of the scoop is shown in phantom.

FIG. 3 is an enlarged cross-sectional view illustrating the construction of the scoop with the brush.

FIG. 4 is a right side view of the scoop.

FIG. 5 is a cross-sectional view of the scoop illustrating the prior art in phantom.

DETAILED DESCRIPTION OF THE INVENTION

Figure 6:
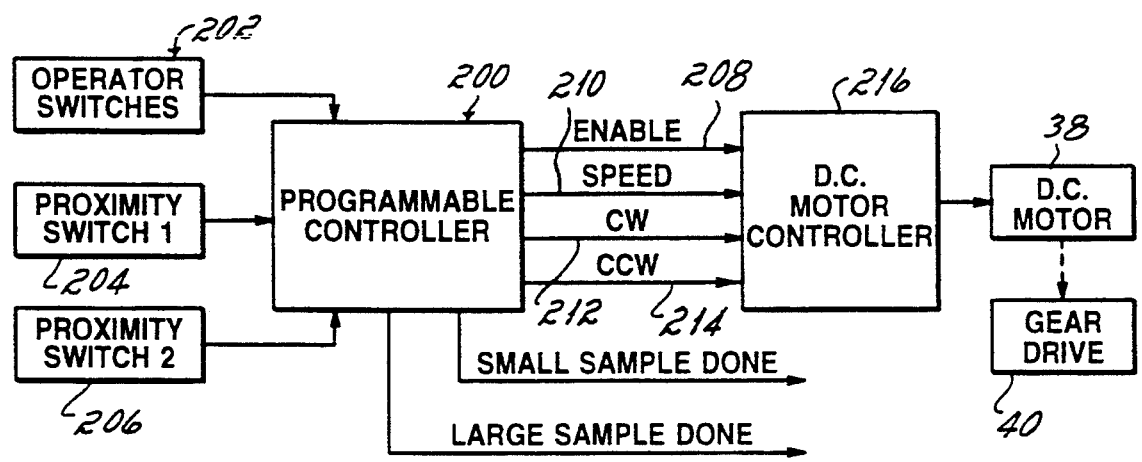
FIG. 6 is a schematic block diagram of the motor drive circuit.

FIGS. 1 and 2 are perspective and center cross-sectional views illustrating the coal sampler 10. Within the sampler 10, a conveyor belt 11 of a continuous conveyor 12 extends in a continuous loop around conveyor pulley 13 mounted in the front end 14 of the frame 16. A second conveyor pulley (not shown) is mounted at the rear end 20 of the frame 16. As is well known, a conveyor drive motor 22 is connected at the front end 14 of the frame 16 and is connected to the conveyor pulley 13 by mechanical coupling 18, thereby providing a power drive for the conveyor belt 11 of the conveyor 12. As is well known, the conveyor pulley at the rear end 20 of the frame 16 may be supported within the frame 16 so as to provide an adjustment of the conveyor tension.

The material, such as coal, to be sampled is discharged from an associated piece of equipment (not shown) which is positioned with respect to the sampler 10 such that the discharged coal is received by an inlet opening 26 on the topside 27 of the sampling machine 10. The inlet contains left and right sidewalls 28, 30, respectively, as well as a rear end wall (not shown). The sidewalls 28, 30 which extend the length of the conveyor 12 to the conveyor pulley 13 function to contain the coal on the top surface of the belt 11 of the moving conveyor 12 which moves the coal from the rear end 20 to the front end 14 of the sampling machine 10. At the front end 14 of the sampling machine 10, the coal drops off the end of the moving conveyor 12, and the force of gravity pulls the coal through a discharge opening (not shown) on the lower side 31 of the sampling machine 10.

A sampling scoop 32 is connected to a rotating drive shaft 34 providing a horizontal axis of rotation 36 which is centrally located above the moving conveyor 12 and parallel to the direction of motion of the conveyor 12 as indicated by direction arrow 24. A DC motor 38 is connected to a gear drive 40, the output of which is the drive shaft 34. Rotation of the motor 38 rotates the sampling scoop 32 through a circular path transverse to the moving conveyor 12. Assume rotation of the sampling scoop 32 is counterclockwise as viewed in FIG. 1. The sampling scoop 32 moves in a first counterclockwise rotational cycle in which the leading edge 44 of the sampling scoop 32 moves transversely across the moving conveyor 12 from left to right. That motion results in a sample volume of coal being collected in a first cavity 45 between a rear side wall 46 and a front side wall 48 of the sampling scoop 32. The side walls 46, 48 are disposed generally parallel to said circular path. An interior end wall or sample pusher wall, 50 of the cavity 45 is effective to push the sampled coal 51, which collected in front of the sample pusher wall 50 and between the sidewalls 46, 48 off the conveyor belt 11 of conveyor 12 and into a first chute, or sample collector, 52 on the right side 54 of the moving conveyor 12. The removed sample is collected in a removable sample collection container 58 located at the bottom of the first chute 52. In a similar manner, rotation of the sampling scoop in an opposite rotational cycle in a clockwise direction, as viewed in FIG. 1, will result in a second sample volume of coal being collected in an opposing cavity 57 in the sampling scoop 32. That second sample volume is pushed off the conveyor belt 11 of moving conveyor 12 and into a second discharge chute, or sample collector, 59 located on the left side 60 of the moving conveyor 12. The sample transferred to the second chute 59 is accumulated in a removable sample collection container (not shown) on the left side 60 of the sampling machine 10.

As shown in FIG. 2 the sampling scoop 32 has a park position, or home position, shown in phantom, preferably at the top most point of its rotation, that is, at the 12 o'clock position. At the home position, the sampling scoop 32 is above the axis of rotation 36, and the sampling scoop axis of symmetry, or centerline, 62 passing through the axis of rotation 36 is approximately vertical. At the near vertical home position, the center of gravity of the sampling scoop 32 is generally over and is supported by the drive shaft 34. Consequently, the mechanical resistance within the gear drive 40 and motor 38 is sufficient to hold the sampling scoop 32 in that upwardly directed vertical home position. Therefore, an independent brake mechanism is not required to hold the sampling scoop at the home position. While the home position is preferably the vertical 12 o'clock position, the home position may be any position on either side of the vertical at which the drive resistance can hold the sampling scoop stable without a separate brake mechanism being required. Therefore, the home position could be ±30° from the vertical.

The curvature of the bottom edge 64 of the sampling scoop 32 is a circular arc that is defined by a radius extending from the axis of rotation 36 along the centerline 62 to the intersection of the centerline 62 with the bottom edge 64. The edge profile of the conveyor changes from a horizontal flat profile to an upwardly directed concave circular profile as the conveyor 12 passes beneath the rotating sampling scoop 32. The circular profile of the conveyor 12 matches the circular bottom edge 64 of the sampling scoop 32, as shown in FIG. 2, thereby avoiding damage to the conveyor as samples are taken. The curvature of the conveyor 12 is designed so that as the sampling scoop 32 sweeps over the top surface 66 of the conveyor belt 11 and of the conveyor 12, there is an approximately constant clearance or separation between the top surface 66 of the conveyor 12 and the bottom edge 64 of the scoop 32. That clearance is approximately 0.125 inches. Therefore, as previously described, as the sampling scoop 32 rotates in a counterclockwise direction, the sample pusher wall 50 is effective to push a sample of coal 51 off the top surface 66 of moving conveyor 12 and into the first chute 52. As shown in FIG. 2, the chutes 52 and 59 have inner-directed walls 68 and 70, respectively, that extend below the respective right and left edges 54 and 60 of the moving conveyor 12. Consequently, all materials pushed off either edge 54, 60 of the moving conveyor 12 will drop into a respective chute 52, 59.

FIGS. 3 and 4 illustrate the detailed construction of the sampling scoop 32. The scoop includes rear and front vertical sidewalls 46 and 48, respectively, disposed generally perpendicular to the direction of motion of the moving conveyor 12. First and second sample pusher walls 50 and 78, respectively, are connected between the rear and front sidewalls 46, 48. The sample pusher walls 50, 78 are straight and flat and have respective first edges 80 and 82 which are disposed outwardly from respective lower edges 84 and 86. Therefore, as shown in FIG. 5, when the sample pusher wall 50 reaches the edge 54 of the moving conveyor 12, the sample pusher wall 50 has a substantially vertical orientation. That substantially vertical orientation provides a more complete and consistent discharge of the sampled volume from sampling scoop 32. Prior sampling scoops do not have the straight sample pusher walls 50, 78 of the present invention; but instead, prior scoops have an end wall which extends radially at the center of the scoop and outward from the scoop, such as the radial wall 79 shown in phantom in FIG. 5. With such a profile, the radial wall 79 provides a less effective discharge of the sampled volume than the straight sample pusher wall 50. Each of the sidewalls 46 and 48 has a bottom edge 64 disposed between first and second side edges 90 and 92, respectively. The first and second sidewalls 46 and 48 are parallel and identical in size and shape; and therefore, their respective side edges 90, 92 and bottom edge 64, are generally parallel. The bottom edges 64 of the sidewalls 46 and 48 are arcuately shaped to correspond to the arcuate shape of the upper surface 66 of the moving conveyor 12. The upper edges 80 and 82 of the respective sample pusher walls 50 and 78 are substantially coincident with the upper extremities of the side edges 90 and 92 of each of the sidewalls 46, 48. Consequently, there is no surface within the cavities 45, 57 of the sampling scoop 32 which is substantially perpendicular to the sample pusher walls 50, 78 of the sampling scoop 32. Referring to FIG. 5, the end wall 79 of prior scoops is shown in phantom and extends upward through the scoop, curves outwardly at approximately a right angle and intersects the upper edges of the side walls. The right angle curve results in intersecting surfaces which form a corner, or pocket, in which material can collect and from which it is difficult to discharge material. The straight sample pusher walls 50, 78 of the present invention have no internal corners or curves, and there is a greater probability that all of the sampled volumes will be discharged.

The sampling scoop 32 has a brush 76 extending approximately 0.125" from its bottom edge 64. The brush 76 is centrally located on the centerline 62 of the sampling scoop 32 and extends the full distance between its sidewalls 46, 48. As the sampling scoop moves over the moving conveyor 12, the lower end of the brush 76 contacts the upper surface 66 of the moving conveyor 12 and is effective to brush or wipe fine particles of coal off the top surface 66 and into one of the chutes 52, 59. The brush 76 is secured in a brush holder 94 by means of two bolts 96 and two nuts 98. The brush 76 is held between first and second extension plates 100 and 102 which are rigidly connected at their other end to mounting plate 104. The brush 76 and extension plates 100, 102 are inserted through an upper opening 106 in the top side 107 of the sampling scoop 32. The brush and extension plates are extended through the sampling scoop 32 until the brush projects through an opening 108 formed between the bottom edges 64 of the sidewalls 46, 48 and the lower edges 84 and 86 of the respective sample pusher walls 50 and 78. Therefore, the brush 76 is sandwiched between the lower edges 84, 86 of sample pusher walls 50 and 78, respectively. The brush holder 94 is secured to the sampling scoop 32 by two bolts 110 and connecting nuts 112. The brush 76 is mounted in and connected to the sampling scoop 32 at points intermediate the sampler pusher walls 50, 78.

With the above construction, the outwardly directed surfaces 116 of the sample pusher walls 50, 78 are free of any projections from said surfaces 116, such as, for example, brush mounting fasteners 96, 98. Referring to FIG. 5, with prior scoop designs, the fasteners 96 holding the brush 76 in the scoop are located on the outer directed surface of the end wall 79. The prior art designs also contained fasteners 81, shown in phantom, on the outer directed surface of wall 79 which mounted to the wall to the scoop. With the present invention, the interior surfaces 114 of the side walls 46, 48 and the outer directed surfaces 116 of the sample pusher walls 50, 78 are straight, smooth and flat; and there are no projections which could collect or accumulate sampled material. Therefore, all of the sampled coal collected in the cavities bounded by the surfaces 114, 116 will be discharged from the sampling scoop 32 and into the chutes 52, 59.

Figure 7:
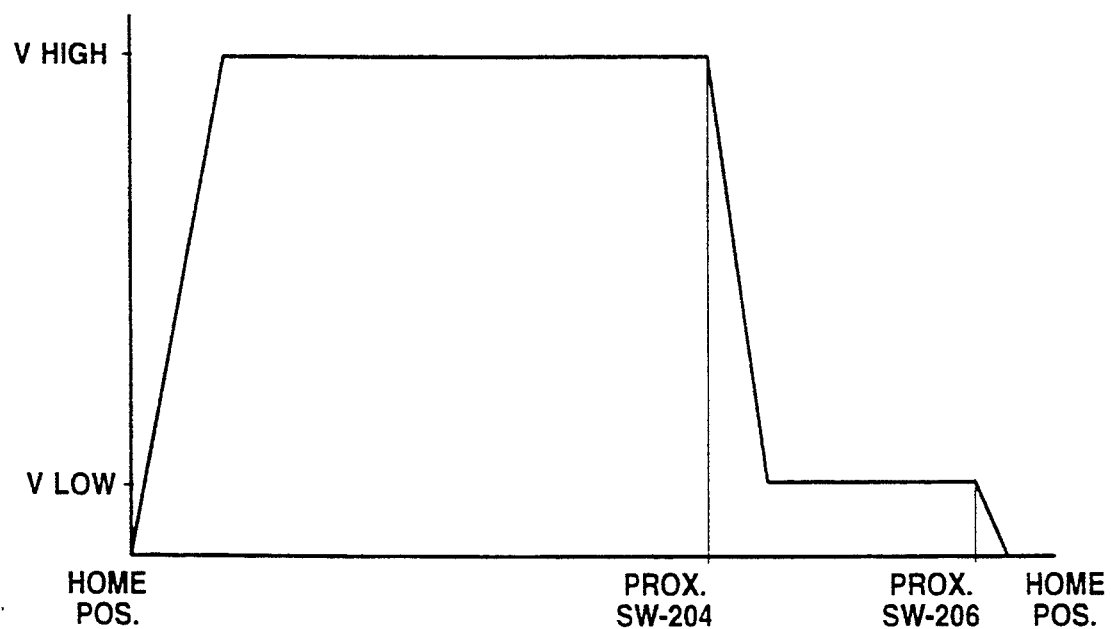
FIG. 7 is a timing diagram illustrating the velocity of the scoop versus its rotational position during a single rotational cycle.

FIG. 7 is a block diagram of the control for the coal sampler 10 illustrated in FIG. 1. A programmable controller 200, such as, for example, an Allen Bradley SLC 500 PLC, commercially available from dealers in Cincinnati, Ohio, is responsive to input signals provided by operator switches 202 and proximity switches 204 and 206. As shown in FIGS. 1 and 2, proximity switches 204, 206 are mounted on an outer directed surface of a wall 120 of housing 118 which is mounted to the frame 16 and encloses the sampling scoop 32. The proximity switches 204, 206 extend through holes 122, 124, respectively, so that the switches are able to detect the position of the sampling scoop 32. The programmable controller produces output signals in response to the input signals and a ladder logic program stored within the controller 200. The programmable controller produces enable, high or low speed, clockwise and counterclockwise output signals on lines 208, 210, 212 and 214, respectively. A DC motor controller 216 is responsive to the output signals to provide the appropriate velocity and direction signals to the DC motor 38. Preferably, the DC motor 38 is a 0.5 HP motor which can be obtained from several suppliers such as Baldor; and the gear drive 40 connected to the DC motor 38 is preferably an SEW Eurodrive gear box, both of which are commercially available from dealers in Cincinnati, Ohio.

In use, there are many different possible sampling cycles, depending on the requirements of the sampling standards. Further, the implementation of any particular sampling cycle for a particular standard will depend on the equipment upstream from the sampler as well as down stream from the sampler. A typical example of a multiple sample situation is the requirement that samples be taken from one side of the conveyor that represent a composite of a total load of coal, for example, 100 rail cars, and that a second sample be taken from the other side of the conveyor which represents a composite of a smaller increments of the total load, for example, 5 rail cars. The timing of the operation of the sampling machine of the present invention will be dependent on the operating cycle of an upstream samplers such as a primary sampler. Assume the upstream primary sampler operates on an intermittent basis and samples a relatively large volume of coal. The downstream secondary sampler may be required to take one or more samples of a single upstream primary sample. Therefore, in a manner well known, as the upstream sample is received by the downstream secondary sampler, a metering gate at the input to the secondary sampler is effective to establish a constant depth of the coal on the moving conveyor 12 thereby guaranteeing that the volume flowrate of coal passing under the sampler is constant.

Knowing the weight and volume requirements of the multiple samples to be collected and further knowing the timing and volume of the upstream sampler, the sample cycle for the secondary sampler can be determined. For example, the programmable controller must know how often to take a sample for the large composite sample and how often to take a sample for the smaller composite sample. Further, the controller must know how many cycles of each sample will result in a complete sample being taken, and the controller should provide an output signal indicating when the large and small composite samples are complete. That signal will indicate that the current sample collection unit is full and should be replaced with an empty unit. With the above information regarding the multiple sampling cycles, the programmable controller can be programmed with the ladder logic program to effect the desired cycle of operation. The controller has the capability of providing a wide range of single unidirectional or multiple bidirectional sampling cycles. Single samples may be taken from either side of the conveyor 12 by rotating the sampling scoop 32 in the appropriate clockwise or counterclockwise direction. Multiple samples may be taken from both sides of the conveyor 12 by alternating clockwise and counterclockwise sampling cycles. Since multiple samples typically require different cumulative sample volumes, the controller 200 has the capability of taking a predetermined number of samples in one direction for each sample taken in the other direction. Further, the ratio of the number of samples taken in one direction to the number of samples taken in the other direction can be changed in the control. Further, the timing or sequence of the sampling in each direction may be changed.

For example, the sampling machine is started in response to a operator actuated cycle start switch or a signal produced from the operation of an upstream sampling machine or other equipment. In response thereto, the conveyor drive motor is started; and timers associated with the large and small composite sample cycles are started. The time period for each timer is determined from the sampling requirements. When the controller 200 detects that a time period has expired, it initiates a large composite or small composite sampling cycle associated with that timer. The controller then checks to determine whether the required number of samples has been taken; and if so, a sample complete output signal is generated. That signal may be used for the manual or automatic exchange of the appropriate sample collection container.

When the controller determines that a sampling cycle is to be executed, it generates the appropriate output signals to cause the DC motor controller 216 to operate the DC motor 38 to rotate the sampling scoop 32 through a rotational cycle from its starting home position through one revolution in the appropriate direction and back to the starting home position. FIG. 7 is a timing diagram that relates rotational velocity of the sampling scoop to rotational position as a result of the programmable controller producing output signals to execute a clockwise or counterclockwise cycle of operation. As shown at the origin of the graph of FIG. 7, the sampling scoop starts at the home position. Assume that the controller activates a sample cycle corresponding to a counterclockwise angular direction sample of operation. The controller will initiate a first rotational cycle by producing an enable output signal on line 208 and a counterclockwise output signal on line 214. The speed output signal on line 210 has two states which represent high and low motor velocities. The controller initially sets the speed output signal to the high velocity state. That results in the DC motor controller 216 producing signals to the DC motor 38 to rotate the sampling scoop 32 in the clockwise direction at the high speed, $V_{HIGH}$. Typically, the high speed signal commands the motor 38 to rotate at 1750 RPM which produces at the output of the gear drive 40 a rotational velocity of the sampling scoop of 38 RPM. The sampling scoop accelerates from a zero velocity to $V_{HIGH}$ and stays at that velocity until the leading edge 44 of the sampling scoop 32 is detected by proximity switch 204. At that point, the programmable controller switches the state of speed output signal on line 210 to the low speed; and DC motor controller 216 applies dynamic braking to decelerate the DC motor 38 and sampling scoop 32 to the $V_{LOW}$ velocity. Typically, the low motor speed is 460 RPM which produces a rotational velocity of the scoop of 10 RPM. That lower velocity is maintained until proximity switch 206 detects the leading edge 44 of the sampling scoop 32 at which point the programmable controller terminates the enable output signal on line 208. Terminating the enable signal causes the DC motor controller 216 to regeneratively brake the DC motor, thereby stopping the sampling scoop at the home position. The operation of the sampling scoop 32 in an opposite second rotational cycle, that is, in a clockwise angular direction, is identical to that just described with the exception that the programmable controller produces a clockwise output signal on line 212. The programmable controller 200 may also sample the input signals from the proximity switches 204, 206 to make sure that the sampling scoop 32 is in the home position. As indicated in FIG. 2, when in the home position, the sampling scoop is located with respect to the proximity switches 204, 206 such that both switches produce an input signal.

While the invention has been set forth by the description of the embodiments in considerable detail, it is not intended to restrict or in any way limit the claims to such detail. Additional advantages and modifications will readily appear to those who are skilled in the art. For example, the sampler could be used to sample other materials than coal which are carried on a moving conveyor. The sampler could be used for tertiary and quaternary sampling. The DC motor could be replaced by other electric motors or pneumatic or hydraulic motors including pneumatic and hydraulic piston and cylinders which are attached to a rack and pinion type drive. The proximity switches could be replaced by any other device that is effective to determine the rotational position of the sampling scoop. Further, it would be possible to directly drive the sampling scoop from the motor instead of utilizing the gear drive. The sampling volumes may be changed by changing the volume of the cavities in the scoop as well as the varying the number of sampling cycles, and the brush may be replaced by other flexible elements that are effective to wipe the upper surface of the conveyor of fine particles not collected by the sampling scoop. The invention in its broadest aspects is therefore not limited to the specific details shown and described. Accordingly, departures may be made from such details without departing from the spirit or scope of the general inventive concept.

What is claimed is:

1. A sampling apparatus for removing a sample volume of a material from a conveyor, the apparatus comprising:
   a frame located adjacent the conveyor;
   drive means mounted on said frame for providing a rotating drive shaft;
   a scoop connected to said drive shaft and rotating about an axis of rotation above the conveyor, said scoop being mounted relative to the conveyor such that rotation of said scoop transverse to conveyor motion is effective to remove the sample volume of the material from the conveyor;
   control means connected to said drive means for selectively commanding said drive means to move said scoop through a circular path during first and second rotational cycles, said first rotational cycle moving said scoop through said circular path from a starting position through a continuous rotation in a first angular direction and stopping said scoop at said starting position, and said second rotational cycle moving said scoop through said circular path from said starting position through a continuous rotation in a second angular direction opposite to said first angular direction and stopping said scoop at said starting position, said starting position being a position of said scoop above said drive shaft such that said drive means holds said scoop at said starting position; and
   first and second sample collectors located on opposite sides of and below the conveyor to receive the sample volumes of the material during said first and second rotational cycles, respectively.

2. The sampling apparatus of claim 1 wherein said scoop includes a pair of spaced parallel vertical sidewalls disposed generally parallel to said circular path, each of said sidewalls having a bottom edge disposed between first and second upwardly extending side edges, said first, second and bottom edges of one of said sidewalls being generally parallel to said first, second and bottom edges of the other of said sidewalls and
   first and second sample pusher walls disposed between said sidewalls, each of the said sample pusher walls having an upper and lower edge, said upper edges being disposed outwardly from said lower edges.

3. The sampling apparatus of claim 2 wherein said bottom edges of said sidewalls are arcuately shaped to correspond to an arcuate shape of an upper surface of the conveyor with which said sampling apparatus is used when the conveyor is viewed in a transverse vertical cross-section.

4. The sampling apparatus of claim 3 wherein said scoop further includes a brush sandwiched between the lower edges of said pusher walls.

5. The sampling apparatus of claim 4 wherein said scoop further includes a bracket supported between said sidewalls and said sample pusher walls for mounting said brush, said sample pusher walls having smooth outer surfaces free of outwardly projecting brush mounting fasteners.

6. The sampling apparatus of claim 5 wherein the upper edges of said sample pusher walls are substantially coincident with the upper extremities of said side edges of said sidewalls.

7. The apparatus of claim 2 wherein said scoop includes a brush secured to said scoop at a point intermediate first and second cavities formed between the first and second sample pusher walls, respectively, and the pair of spaced, parallel, vertical side walls.

8. The sampling apparatus of claim 2 wherein each of said first and second sample pusher walls having a substantially vertically orientation when each of said sample pusher walls is located adjacent an edge of the conveyor.

9. The sampling apparatus of claim 1 wherein said scoop further comprises a lower edge with an arcuate shape, said arcuate shape being defined by a radius extending from said axis of rotation to said lower surface.

10. The sampling apparatus of claim 9 wherein the conveyor has said arcuate shape where said scoop passes above the conveyor, thereby maintaining an approximately constant distance separating the conveyor and said lower edge of said scoop as said scoop moves through each of said rotational cycles.

11. The sampling apparatus of claim 10 wherein said scoop further comprises a brush extending from said lower edge whereby said brush contacts the conveyor as said scoop passes above the conveyor.

12. The sampling apparatus of claim 1 wherein said control means commands each of said first and second rotational cycles of operation by producing a first velocity signal commanding said drive means to move said scoop at a high velocity from said starting position through a first rotational increment;

a second velocity signal commanding said drive means to move said scoop at a low velocity through a second rotational increment back to said starting position; and a third signal commanding the said drive means to stop said scoop at said starting position, thereby ending said rotational cycle of operation.

13. The sampling apparatus of claim 12 wherein said apparatus further comprises:

first means for detecting said first rotational increment of said scoop; and second means for detecting said second rotational increment of said scoop.

14. The sampling apparatus of claim 13 wherein said apparatus further comprises:

a first proximity switch for producing a first position signal in response to said scoop moving through said first rotational increment; and a second proximity switch for producing a second position signal in response to said scoop moving through said second rotational increment.

15. The sampling apparatus of claim 14 wherein said first rotational cycle moves a first sample volume of said material off one side of the conveyor into a first chute for collecting said first sample volume and said second rotational cycle moves a second sample volume off an opposite side of the conveyor into a second chute for collecting said second sample volume.

16. The sampling apparatus of claim 15 wherein said control means moves said scoop through a first predetermined number of first rotational cycles to collect said first predetermined number of said first sample volumes and moves said scoop through a second predetermined number of second rotational cycles to collect a second predetermined number of said second sample volumes.

17. The sampling apparatus of claim 16 wherein said drive means further comprises a DC motor with regenerative braking.

18. The sampling apparatus of claim 17 wherein said control means applies dynamic braking to said DC motor during motion of said scoop through said second rotational increment and regenerative braking to stop said scoop.

19. The sampling apparatus of claim 1 wherein said drive means has a mechanical resistance for holding said scoop in said starting position without requiring a brake mechanism.

* * * * *